(12) United States Patent
Iihoshi et al.

(10) Patent No.: US 7,752,837 B2
(45) Date of Patent: Jul. 13, 2010

(54) DIAGNOSIS APPARATUS FOR INTERNAL COMBUSTION ENGINE

(75) Inventors: Yoichi Iihoshi, Tsuchiura (JP); Shin Yamauchi, Hitachinaka (JP); Toshio Hori, Hitachinaka (JP); Yoshikuni Kurashima, Mito (JP)

(73) Assignee: Hitachi, Ltd., Tokyo (JP)

( * ) Notice: Subject to any disclaimer, the term of this patent is extended or adjusted under 35 U.S.C. 154(b) by 300 days.

(21) Appl. No.: 11/767,654

(22) Filed: Jun. 25, 2007

(65) Prior Publication Data

US 2007/0250230 A1 Oct. 25, 2007

Related U.S. Application Data

(62) Division of application No. 11/206,793, filed on Aug. 19, 2005, now Pat. No. 7,254,474.

(30) Foreign Application Priority Data

Feb. 24, 2005 (JP) ............................. 2005-048166

(51) Int. Cl.
F01N 3/00 (2006.01)
(52) U.S. Cl. .................. 60/277; 60/274; 60/276; 123/688; 123/690; 701/107; 701/109
(58) Field of Classification Search ................... 60/274, 60/276, 277, 285; 123/688, 690; 701/107, 701/109, 114
See application file for complete search history.

(56) References Cited

U.S. PATENT DOCUMENTS

| | | | | |
|---|---|---|---|---|
| 5,396,766 A | * | 3/1995 | Sato et al. | ...................... 60/276 |
| 5,400,592 A | | 3/1995 | Mukaihira et al. | ............ 60/274 |
| 5,758,632 A | | 6/1998 | Yamashita et al. | |
| 5,832,724 A | * | 11/1998 | Watanabe et al. | ............. 60/276 |
| 6,009,866 A | | 1/2000 | Sagisaka et al. | ............. 123/681 |
| 6,138,638 A | | 10/2000 | Morikawa | .................... 123/295 |
| 6,287,453 B1 | | 9/2001 | Rosel et al. | |
| 6,371,096 B1 | | 4/2002 | Ohsaki et al. | |
| 6,470,868 B2 | | 10/2002 | Nakagawa et al. | .......... 123/673 |
| 6,698,186 B2 | * | 3/2004 | Ueno et al. | .................... 60/277 |
| 6,898,927 B2 | * | 5/2005 | Morinaga et al. | ............. 60/284 |
| 6,904,792 B2 | | 6/2005 | Wakahara | .................. 73/118.1 |

(Continued)

FOREIGN PATENT DOCUMENTS

DE    43 31 153 A1    3/1994

(Continued)

OTHER PUBLICATIONS 2 sheets of Form PTO-1449 and 1 sheet of Form PTO-892.

(Continued)

*Primary Examiner*—Binh Q Tran
(74) *Attorney, Agent, or Firm*—Crowell & Moring, LLP

(57) ABSTRACT

In a diagnosis apparatus for an internal combustion engine which determines the abnormality of a linear A/F sensor which is disposed on the upstream side of a catalyst of the engine and detects the A/F of exhaust gas, the apparatus includes a response/gain deterioration detection unit that separately detects the response deterioration in which the response of the linear A/F sensor is delayed and the gain deterioration in which the detection sensitivity of the linear A/F sensor is abnormal.

9 Claims, 15 Drawing Sheets

U.S. PATENT DOCUMENTS 6,978,203 B2 * 12/2005 Yasui et al. .................. 701/101

FOREIGN PATENT DOCUMENTS

| JP | 4-36651 A | 2/1992 |
| JP | 7-145751 A | 6/1995 |
| JP | 8-22051 | 1/1996 |
| JP | 8-220051 A | 8/1996 |
| JP | 10-176578 A | 6/1998 |
| JP | 2004-204772 A | 7/2004 |

OTHER PUBLICATIONS

European Search Report dated Nov. 24, 2005 (six (6) pages).
Japanese Office Action dated Oct. 7, 2008 (three (3) pages).

* cited by examiner

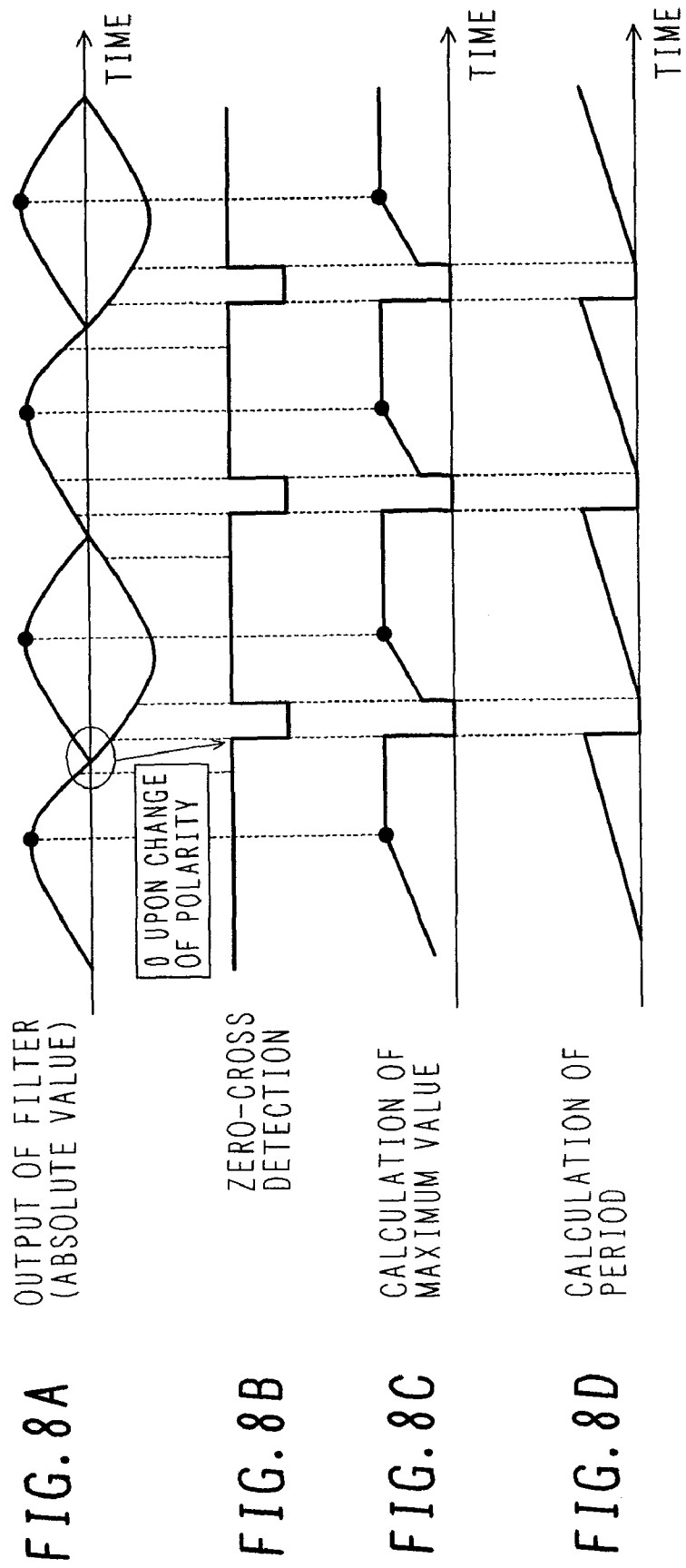

DIAGNOSIS APPARATUS FOR INTERNAL COMBUSTION ENGINE

This application is a divisional of U.S. patent application Ser. No. 11/206,793, filed Aug. 19, 2005, the entire disclosure of which is incorporated herein by reference, which in turn claims priority under 35 U.S.C. §119 of prior Japanese application no. 2005-048166, filed Feb. 24, 2005.

BACKGROUND OF THE INVENTION

1. Field of the Invention

The present invention relates to a diagnosis apparatus for an internal combustion engine which detects abnormality of a linear air-fuel ratio (A/F) sensor for detecting an A/F of exhaust gas of the engine.

2. Description of the Related Art

An exhaust system in which a catalyst is provided at the exhaust pipe of the engine, and an A/F sensor for detecting components of the exhaust gas is attached on each of the upstream and downstream sides of the catalyst, whereby an amount of fuel is corrected based on the detected values of these sensors thereby to efficiently purify the exhaust gas by the catalyst, is known. Since the efficiency of the exhaust system depends on the purification efficiency of the catalyst and the efficiencies of the A/F sensors, there is provided with a diagnosis apparatus for monitoring these efficiencies.

Thus, an example of the method for diagnosing the A/F sensor on the upstream side of the catalyst is proposed, for example, by JP-A-8-220051, in which the response time of the upstream-side A/F sensor is monitored at the time of forcedly changing the A/F.

SUMMARY OF THE INVENTION

The conventional A/F sensor can only determine whether the A/F is richer or leaner as compared with the stoichiometric A/F at which the purification efficiency of the catalyst is best. On the other hand, the linear A/F sensor can detect a deviation value of the A/F on both the rich and lean sides with respect to the stoichiometric A/F, whereby more precise A/F feedback control can be realized by using the linear A/F sensor. There are two major deterioration modes of the linear A/F sensor. The first mode is the response deterioration which is a failure that the response delays as compared with the normal state due to clogging etc. of the sensor. The second mode is the gain deterioration which is a failure that the response gain becomes smaller or larger as compared with the normal state due to the poisoning of a sensor element or the abnormality of a current detection circuit. Each of the response deterioration and the gain deterioration becomes a cause for raising the deterioration of the exhaust gas due to the erroneous determination of the catalyst diagnosis is and the abnormality of the A/F feedback control.

However, JP-A-8-220051 relates to the diagnosis method which only detects the abnormality of the response delay (response deterioration) of the upstream-side A/F sensor, and does not take sufficient consideration as to the abnormality of the detection sensibility (gain deterioration) of the linear A/F sensor for linearly detecting the A/F of the exhaust gas.

The present invention has been made in view of such circumstances, and an object of the present invention is to provide a diagnosis apparatus for an internal combustion engine which separately detects the response deterioration and the gain deterioration of a linear A/F sensor and prevents the deterioration of the exhaust gas and the erroneous diagnosis at the time of the abnormality of the sensor.

In order to attain the aforesaid object, the diagnosis apparatus for an internal combustion engine according to the present invention includes a response/gain deterioration detection unit that separately detects the response deterioration in which the response of the linear A/F sensor is abnormal and the gain deterioration in which the detection sensitivity of the linear A/F sensor is abnormal. The diagnosis apparatus further includes a diagnosis signal generation unit which applies A/F deviation whose frequency (equal to or lower than 1 Hz) is lower than that of the normal A/F control during the diagnosis of the linear A/F sensor.

Further, the present invention employs the A/F deviation by the diagnosis signal generation unit also for the catalyst diagnosis.

Furthermore, the present invention includes an abnormality alarm unit which notifies the gain deterioration of the linear A/F sensor to a driver.

According to the present invention, the degradation of the exhaust gas and the erroneous diagnosis due to the failure of the linear A/F sensor can be prevented. Further, according to the present invention, the degradation of the exhaust gas and the erroneous diagnosis of the catalyst diagnosis due to the failure of the linear A/F sensor can be prevented. Furthermore, according to the present invention, the occurrence of the abnormality can be notified to a driver even when only the gain deterioration is generated.

BRIEF DESCRIPTION OF THE DRAWINGS

FIGS. 8A to 8D are diagrams showing an example of the timing chart shown in FIGS. 7A and 7B.

DETAILED DESCRIPTION OF THE INVENTION

The embodiments of the present invention will be explained with reference to the accompanying drawings.

Figure 1:
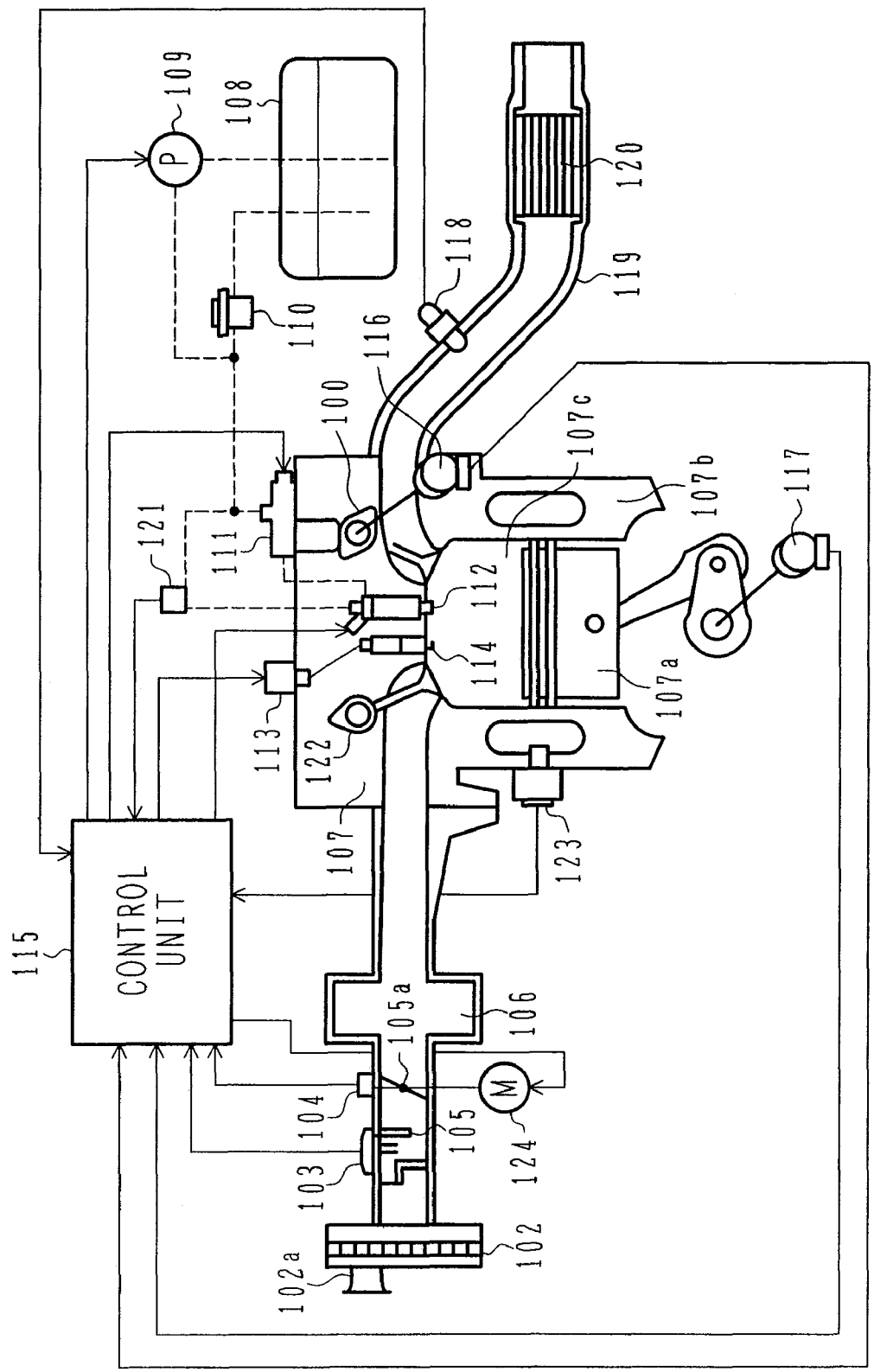
FIG. 1 is a diagram showing the entire configuration of the control system of a gasoline direct injection engine.

FIG. 1 is a diagram showing the entire configuration of the control system of a gasoline direct injection engine 107. Suction air to be introduced into cylinders 107c is taken from the inlet portion 102a of an air cleaner 102 and supplied to a collector 106 through an air flow sensor 103 as one of operating state measuring units of the engine and a throttle body 105 in which an electric control throttle valve 105a for controlling a flow rata of the suction air is housed. The air flow sensor 103 outputs a signal representing the suction-air flow rate to a control unit 115 serving as an engine control apparatus.

At the throttle body 105, a throttle sensor 104 is attached which serves as one of the operating state measuring units of the engine and detects the opening degree of the electric control throttle valve 105a. The sensor 104 outputs a signal representing the opening degree of the throttle valve to the control unit 115.

The air sucked into the collector 106 is distributed into intake manifolds 101 coupled to the cylinders 107b of the engine 107 and then introduced into corresponding combustion chambers 107c of the cylinders 107b, respectively.

Fuel such as gasoline supplied from a fuel tank 108 is primarily pressurized by a fuel pump 109, then adjusted in its pressure to a constant value by a fuel pressure regulator 110, then secondarily pressurized to a high pressure by a high-pressure fuel pump 111 and supplied to a common rail.

The high-pressure fuel is injected into the combustion chambers 107c from injectors 112 provided at the respective cylinders 107b. The fuel injected into the combustion chambers 107c is ignited by ignition plugs 114 in response to ignition signals which voltages are made high by ignition coils 113, respectively.

A cam angle sensor 116 attached to the cam shaft of the exhaust valve outputs a signal for detecting the phase of the cam shaft to the control unit 115. The cam angle sensor may be attached to the cam shaft of the suction valve side. A crank angle sensor 117 for detecting the rotation and phase of the crank shaft of the engine is provided on the crank shaft. The output of the crank angle sensor is supplied to the control unit 115.

An A/F sensor 118 provided on the upstream side of a catalyst 120 within an exhaust pipe 119 detects the density of oxygen within the exhaust gas and outputs a detection signal to the control unit 115. Although the explanation is made as to the case where the present invention is applied to a gasoline direct injection engine, the present invention is not limited thereto and may be applied to a port-injection engine in which an injector 112 is attached to a suction port.

First Embodiment

The embodiment of the present invention will be explained with reference to FIGS. 2 to 9.

Figure 2:
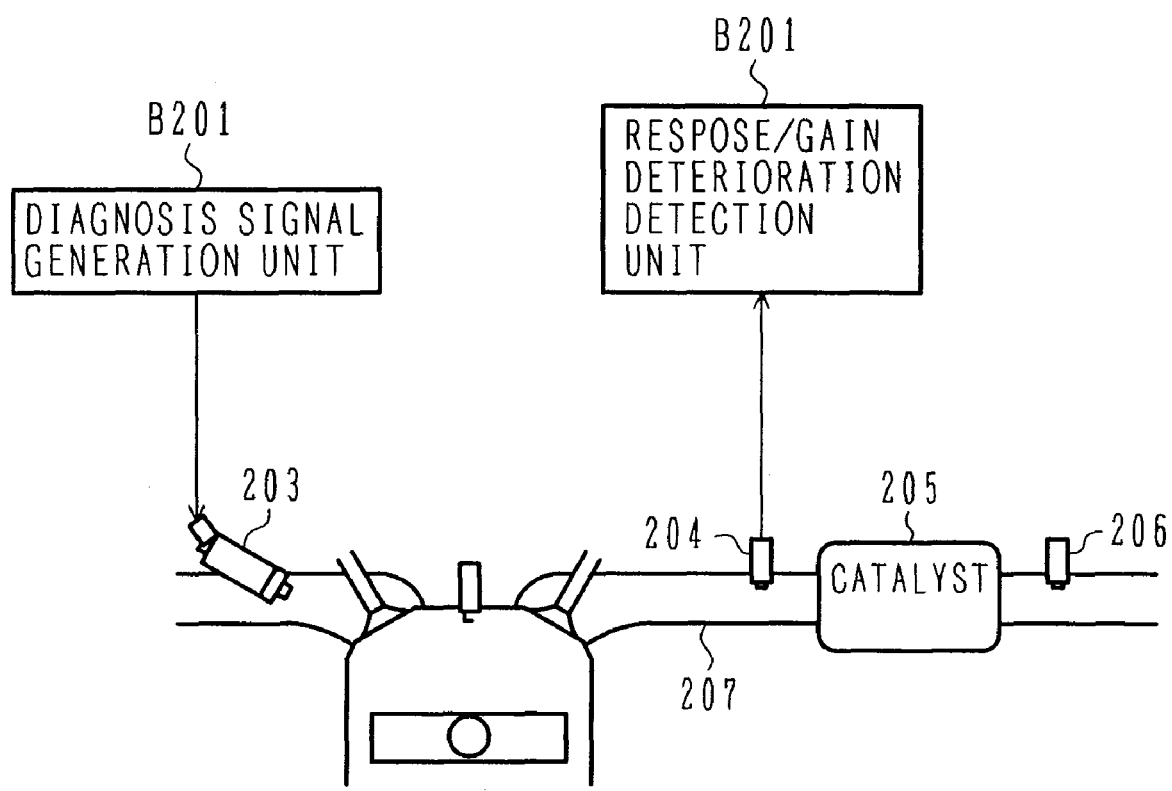
FIG. 2 is a diagram schematically showing the diagnosis apparatus for the engine according to an embodiment of the present invention.

FIG. 2 schematically shows the diagnosis apparatus for the engine which detects the abnormality of the linear A/F sensor (LAF sensor) provided on the upstream side of the catalyst. An injector 203 is provided at the suction port. A linear A/F sensor 204 is provided on the upstream side of a catalyst disposed on the way of an exhaust pipe 207. An A/F sensor 206 is provided on the downstream side of the catalyst 205. In the normal A/F control (a control mode for controlling an A/F), the fuel is increased and decreased at the frequency in a range which is larger than 1 Hz and equal to or smaller than 3 Hz. The frequency of the A/F control will be explained. In order to set the A/F within the engine to a predetermined A/F, the control unit 115 in FIG. 1 detects the A/F within the exhaust pipe based on the output of the linear A/F sensor disposed within the exhaust pipe thereby to adjust an amount of fuel supplied from the injector based on the detected A/F. The frequency of the increase/decrease of the amount of fuel supplied from the injector at this time is the frequency of the A/F control.

The diagnosis apparatus of the embodiment is arranged in a manner that the linear A/F sensor detects the A/F of the exhaust gas at the time where the fuel amount is increased/decreased slightly at the frequency of 1 Hz or less by the diagnosis signal generation unit B201 (diagnosis mode), and the response/gain deterioration detection unit B202 detects separately the response deterioration and the gain deterioration. Preferably, the low frequency range of the diagnosis mode is in a range of 0.3 Hz or more in view of the deterioration of the exhaust gas and the operability.

Figure 3:
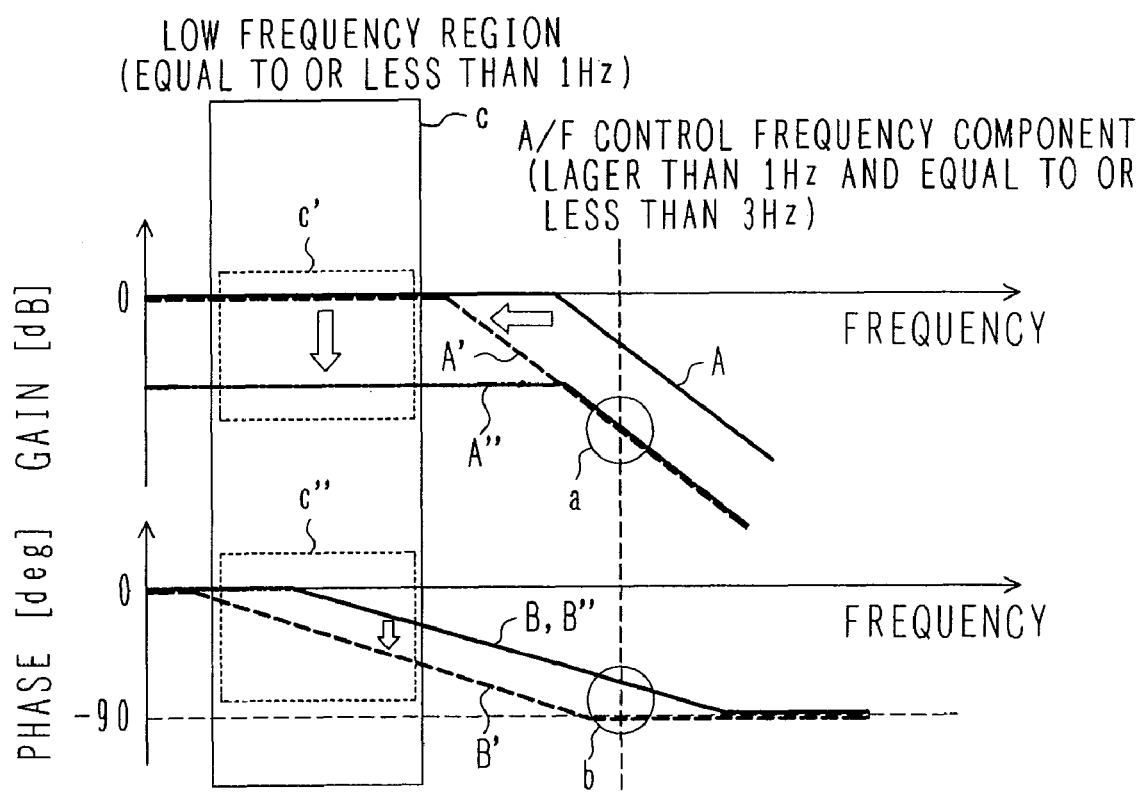
FIG. 3 is a diagram for explaining the principle of the embodiment.

Next, the principle of the diagnosis in this embodiment will be explained. FIG. 3 shows the gain characteristics and the phase characteristics of the linear A/F sensor, respectively. In FIG. 3, A, A' and A" represent the gain characteristics at the time of the normal state, the response deterioration state and the gain deterioration state of the linear A/F sensor, respectively. In FIG. 3, B, B' and B" represent the phase characteristics at the time of the normal state, the response deterioration state and the gain deterioration state of the linear A/F sensor, respectively. That is, the response deterioration represents a phenomenon that the gain characteristics shifts to the left side in FIG. 3 (the low-frequency side) from the normal state (A→A') and the phase delays from the normal state (B→B') (see FIG. 3). In contrast, the gain deterioration represents a phenomenon that the gain characteristic shifts to the lower side in FIG. 3 (the low-gain side) from the normal state (A→A") but the phase does not change from the normal state (B, B") (see FIG. 3). When the deterioration detection is made at the frequency (in a range which is larger than 1 Hz and equal to or smaller than 3 Hz) used in the normal A/F control, the gain changes in both the response deterioration and the gain deterioration, so that it is possible to discriminate between the normal state and the deterioration state. However, it is quite difficult to discriminate between the response deterioration and the gain deterioration (see a in FIG. 3). In contrast, when the deterioration detection is made at the low frequency range c (for example, smaller than 1 Hz), the gain reduces only at the time of the gain deterioration and the phase delays only at the time of the response deterioration. Thus, the response deterioration and the gain deterioration can be easily detected separately by notifying a gain range c' for the detection of the gain deterioration and notifying a phase range c" for the detection of the response deterioration.

Figure 4A:
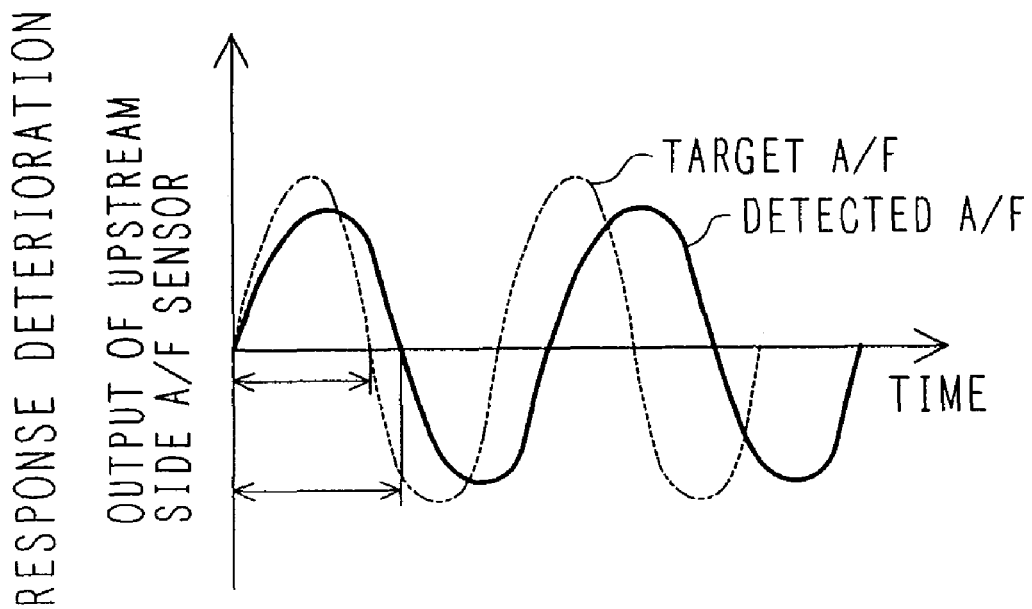
FIGS. 4A and 4B are diagrams showing an example of deterioration indexes according to the embodiment.
Figure 4B:
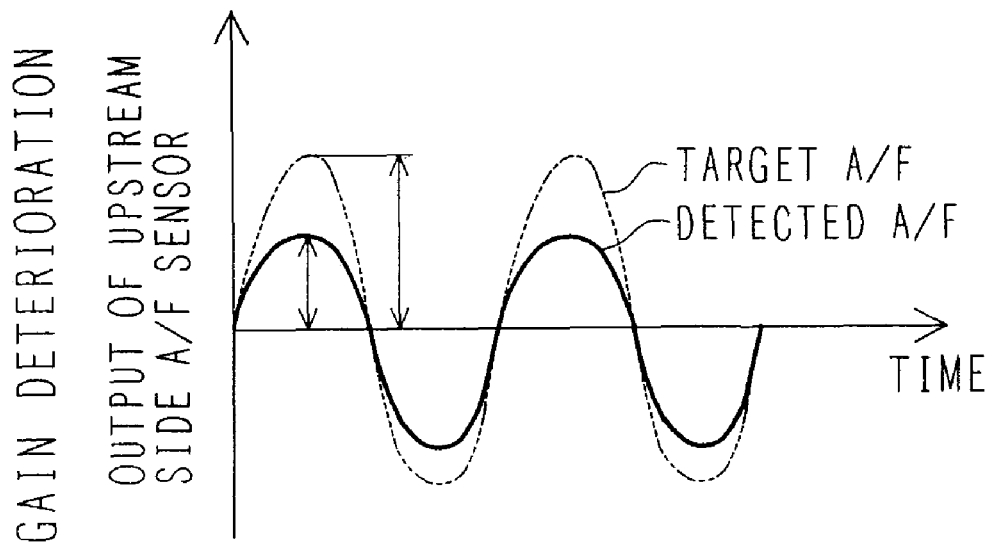

FIGS. 4A and 4B show an example of deterioration indexes based on the principle of FIGS. 3A and 3B. The A/F is vibrated periodically at the low frequency range by the diagnosis signal generation unit shown in FIG. 2. In this case, in the response deterioration, the period of the A/F detected by the A/F sensor (detected A/F) becomes longer than the period of the A/F (target A/F) given by the diagnosis signal generation unit due to the phase delay. On the other hand, in the case where the gain reduces due to the gain deterioration, the amplitude of the detected A/F becomes smaller as compared with the amplitude of the target A/F due to the gain reduction. Thus, a ratio between the period of the detected A/F and the period of the target A/F is used as the response deterioration index(response deterioration index=period of the detected A/F/period of the target A/F). In contrast, a ratio between the peak value of the amplitude of the detected A/F and the peak value of the amplitude of the target A/F is used as the gain deterioration index (gain deterioration index=peak value of the amplitude of the detected A/F/peak value of the amplitude of the target A/F). Thus, the response deterioration and the gain deterioration can be easily separated and diagnosed in accordance with the deterioration degree of the response deterioration and the gain deterioration by using these two indexes.

Figure 5:
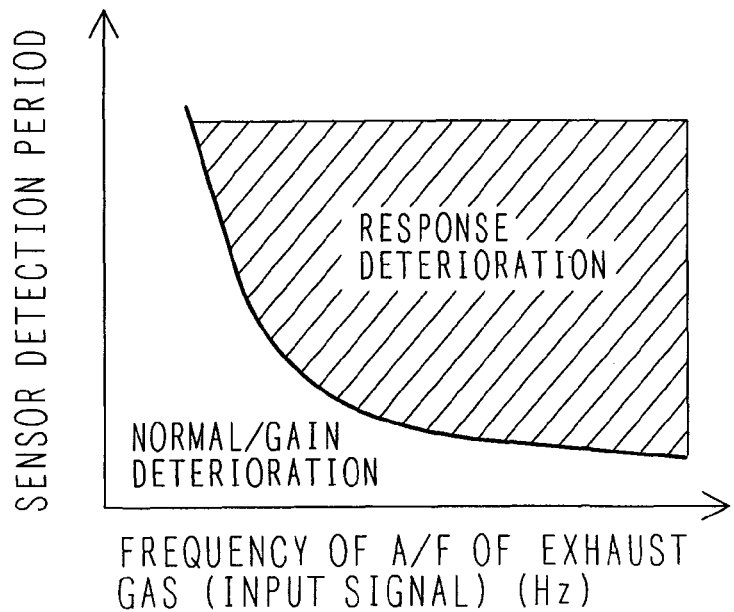
FIG. 5 is a diagram showing an example of the conventional diagnosis method.
Figure 6:
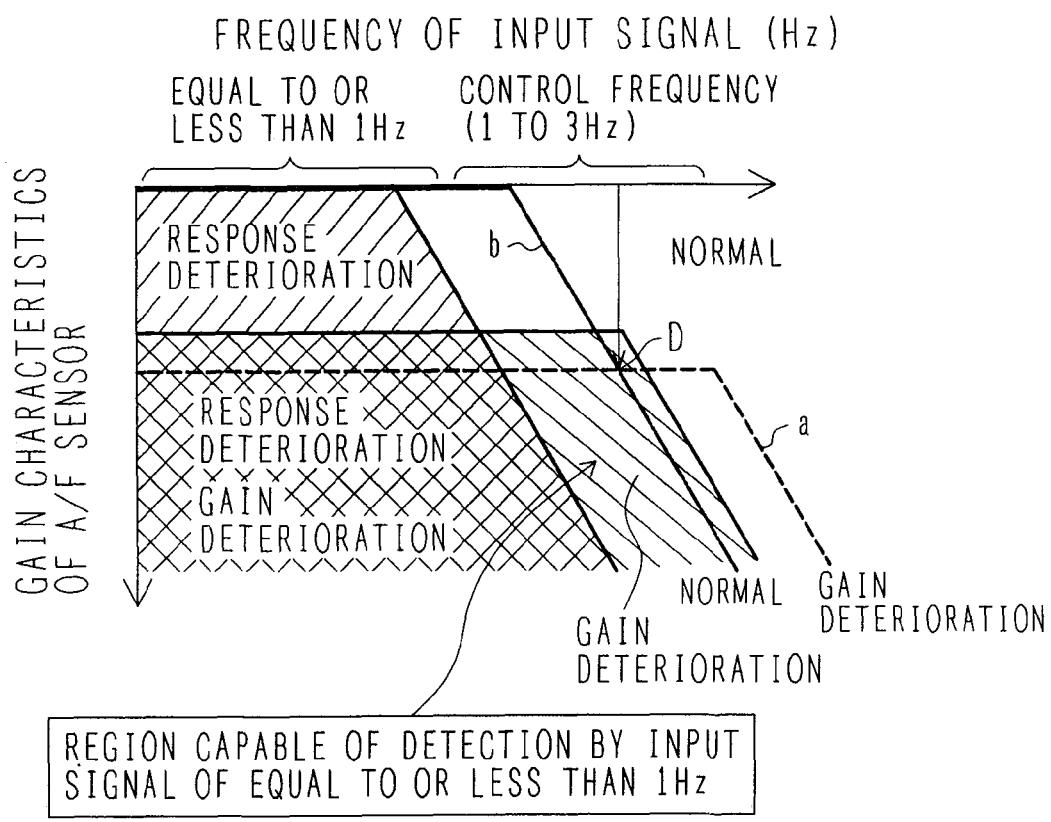
FIG. 6 is a diagram for explaining the feature of the embodiment.

Next, the comparison will be made between the conventional diagnosis of the A/F sensor (O2 sensor) and the diagnosis of the linear A/F sensor according to the embodiment. According to the conventional diagnosis of the A/F sensor, since the O2 sensor is subjected to the diagnosis, the deterioration detection is made only for the response deterioration. For example, as shown in FIG. 5, the abscissa is set to represent the frequency of the A/F of the exhaust gas (input signal) generated by the diagnosis signal generation unit B201, whilst the ordinate is set to represent the period of the detected A/F actually detected by the A/F sensor disposed in the exhaust pipe. It is determined that the sensor is in the response deterioration state when a ratio of the period of the detected A/F actually detected by the A/F sensor disposed in the exhaust pipe represented by the ordinate with respect to the frequency of the A/F of the exhaust gas (input signal) generated by the diagnosis signal generation unit B201 represented by the abscissa is a predetermined value or more. However, according to the conventional method, it is difficult to detect the gain deterioration since the period does not change between the normal state and the deterioration state. On the other hand, according to the conventional technique, there is a method of detecting the deterioration based on the gain characteristics, e. g., a method of detecting the deterioration based on the deterioration of the gain characteristics at the control frequency (in a range which is larger than 1 Hz and equal to or smaller than 3 Hz). However, according to this conventional method, as shown in FIG. 6, there is a possibility that the sensor is determined to be in the gain deterioration state despite that the sensor is normal. In FIG. 6, b represents the range where the sensor is within the normal range despite that there arises the response deterioration slightly. In contrast, a represents the range where the sensor is within the abnormal range since the gain deterioration is remarkable despite that there does not arise any response deterioration. Thus, the gain deterioration can not be detected correctly in a certain range of a cross point D at which the region a where only the gain deterioration appears crosses with the region b where the sensor is normal. In order to detect such a gain deterioration, the input signal of the low frequency (equal to or less than 1 Hz) is necessary. According to this embodiment, the gain deterioration, which can not be detected by the conventional method, can be detected by notifying the gain characteristics of the low frequency range.

Figure 7A:
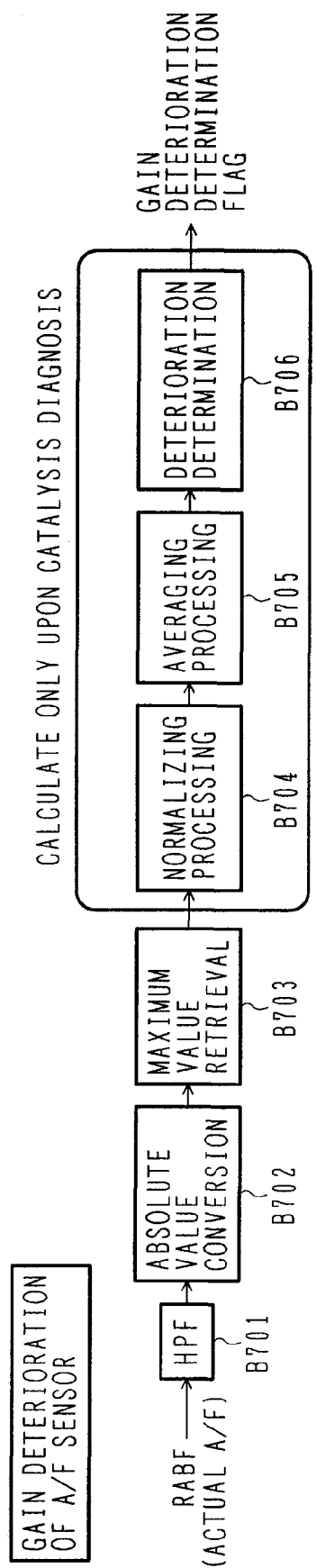
FIGS. 7A and 7B are diagrams showing an example of block diagrams representing the procedure for realizing the embodiment.
Figure 7B:
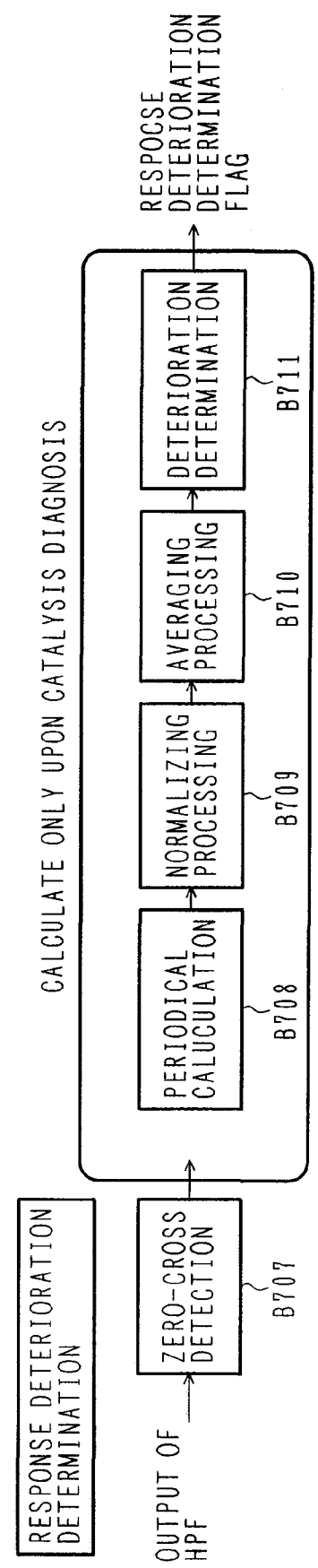

FIGS. 7A and 7B show an example of block diagrams representing the procedure for realizing the gain deterioration determination and the response deterioration determination, respectively. In the gain deterioration determination shown in FIG. 7A, an RABF (actual A/F) is passed through a high pass filter at B701 thereby to remove a DC component and a drift component therefrom. Next, the output of the HPF is converted into an absolute value at B702, and the maximum value is retrieved at B703 thereby to calculate the peak value of the detected A/F. Then, the gain deterioration index shown in FIG. 4B is calculated by the normalizing processing at B704, and noise is removed by the averaging processing at B705. Then, at B706, it is determined to be the gain deterioration when the average gain deterioration index outputted from B705 is outside of the predetermined range thereby to set a gain deterioration determination flag. On the other hand, in the response deterioration determination shown in FIG. 7B, the output of the high pass filter at B701 is subjected to the zero-cross detection by the zero-cross detection at B707. Then, the period of the zero-cross detection is calculated by the periodical calculation at B708. Then, the response deterioration index shown in FIG. 4A is calculated by the normalizing processing at B709, and noise is removed by the averaging processing at B710. Then, at B711, it is determined to be the response deterioration when the average response deterioration index outputted from B710 is larger than the predetermined value thereby to set a response deterioration determination flag.

FIGS. 8A to 8D are an example of the timing chart shown in FIGS. 7A and 7B, which represents a state where the zero-cross of the output of the filter is detected, and the maximum value and period are calculated in response to the zero-cross detection serving as a trigger. In this example, since the deterioration index calculation can be performed twice per one period, the deterioration can be detected with a shorter time period.

Figure 9A:
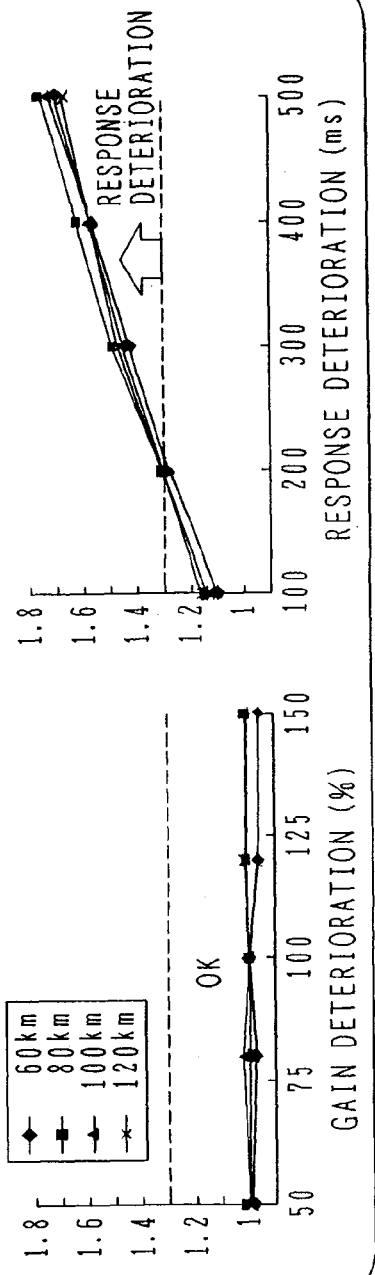
FIGS. 9A and 9B are diagrams showing an example of the deterioration detection according to the embodiment.
Figure 9B:
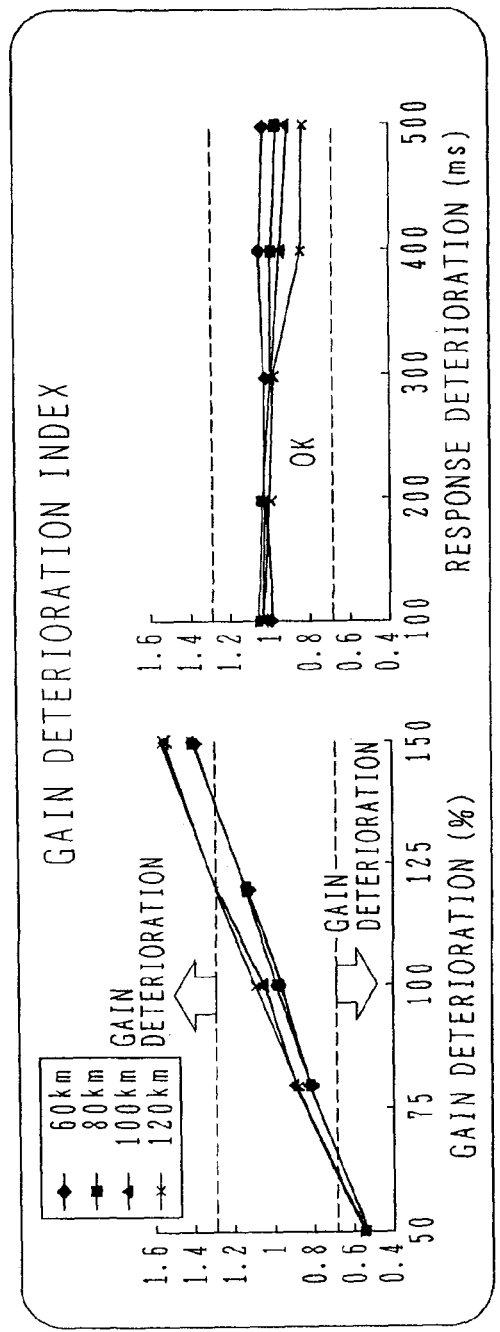

FIGS. 9A and 9B show an example which represents the case where the deterioration of the linear A/F sensor is actually detected by the block diagrams shown in FIGS. 7A and 7B at various vehicle speeds. FIG. 9A shows the gain deterioration indexes when the gain deterioration or the response deterioration exits. On the other hand, FIG. 9B shows the response deterioration indexes when the gain deterioration or the response deterioration exits. When the gain deterioration represented at the abscissa at each left side figure in FIGS. 9A and 9B is 100%, it is represented that the linear A/F sensor has no gain deterioration. In contrast, when the response deterioration represented at the abscissa at each right side figure in FIGS. 9A and 9B is about 100 ms, it is represented that the linear A/F sensor has no response deterioration. As a result, when the determination criterion for determining the gain deterioration is set in a range of 0.7 to 1.3, the gain deterioration of 50% or less or 150% or more can be detected as the gain deterioration. Similarly, when the determination criterion for determining the response deterioration is set to 1.3, the response deterioration of 300 ms or more can be detected as the response deterioration. In this case, it can be confirmed that although the response deterioration index increases as the degree of the response deterioration increases, the response deterioration index is not sensitive as to the gain deterioration. Further, it can be confirmed that although the gain deterioration index increases or decreases in accordance with the degree of the gain deterioration, the gain deterioration index is not sensitive as to the response deterioration.

Figure 10B:
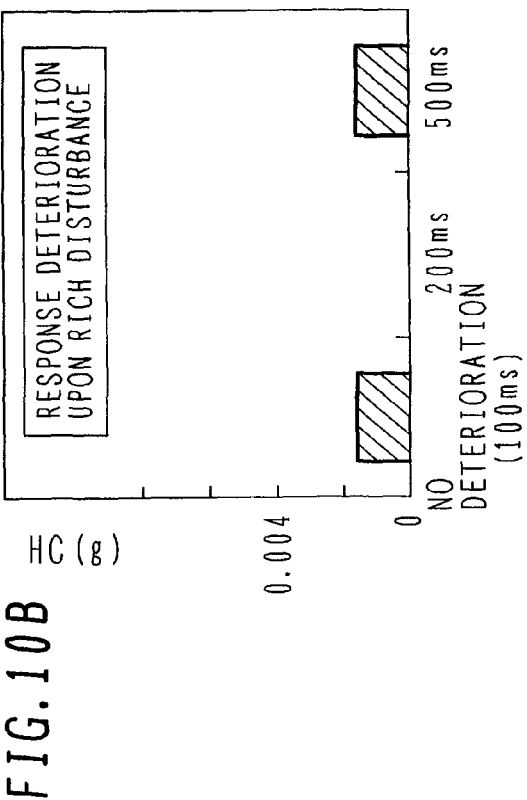
FIGS. 10A to 10D are diagrams showing the experimental result representing the relation between the sensor deterioration and the exhaust gas deterioration.
Figure 10D:
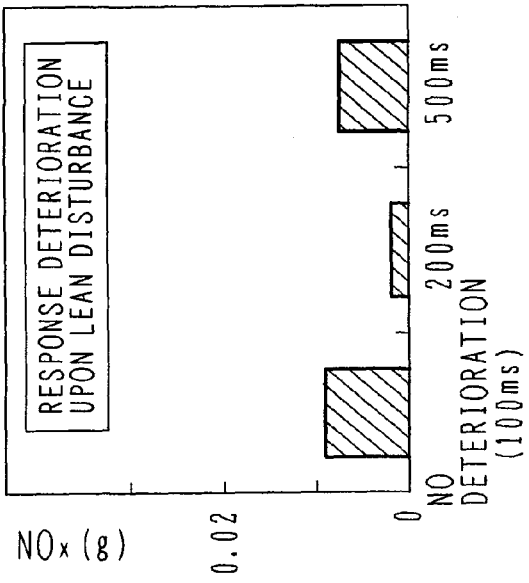
Figure 10A:
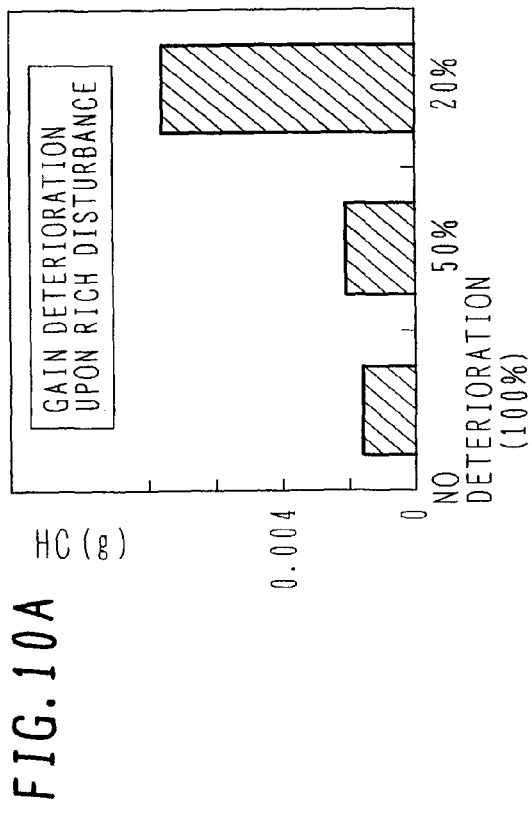
Figure 10C:
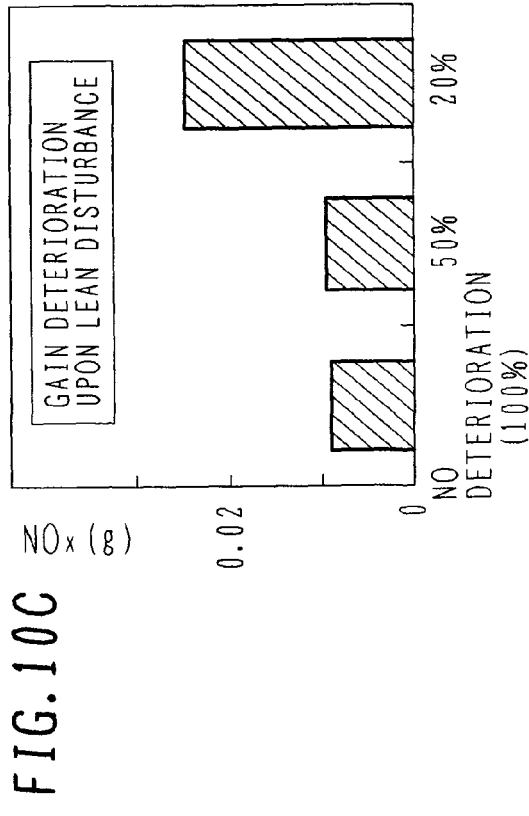

Next, FIGS. 10A to 10D show the experimental result representing the relation between the sensor deterioration and the exhaust gas deterioration. That is, FIGS. 10A to 10D show the deterioration characteristics of the exhaust gas at the time of applying the rich or lean step disturbance during the feedback control of the A/F using the linear A/F sensor. In this case, the catalyst disposed in the exhaust pipe is normal. FIGS. 10A and 10C show the result of the gain deterioration and FIGS. 10B and 10D show the result of the response deterioration. The response deterioration characteristics was not sensitive for the step disturbance, whilst the gain deterioration characteristics was degraded for the step disturbance in a manner that HC density became three times and NOx density became twice as compared with the state before the application of the step disturbance. The reason of this degradation is considered that the feedback control using the linear A/F sensor is performed based on a deviation, but the deviation takes a value different from the actual value due to the gain deterioration, so that the exhaust gas was degraded. However, since the catalyst was normal, this degradation of the exhaust gas was caused by the gain deterioration of the sensor. Thus, when the output of the sensor is corrected in accordance with the degree of the deterioration, the degradation of the exhaust gas due to the gain deterioration can be prevented.

Figure 11:
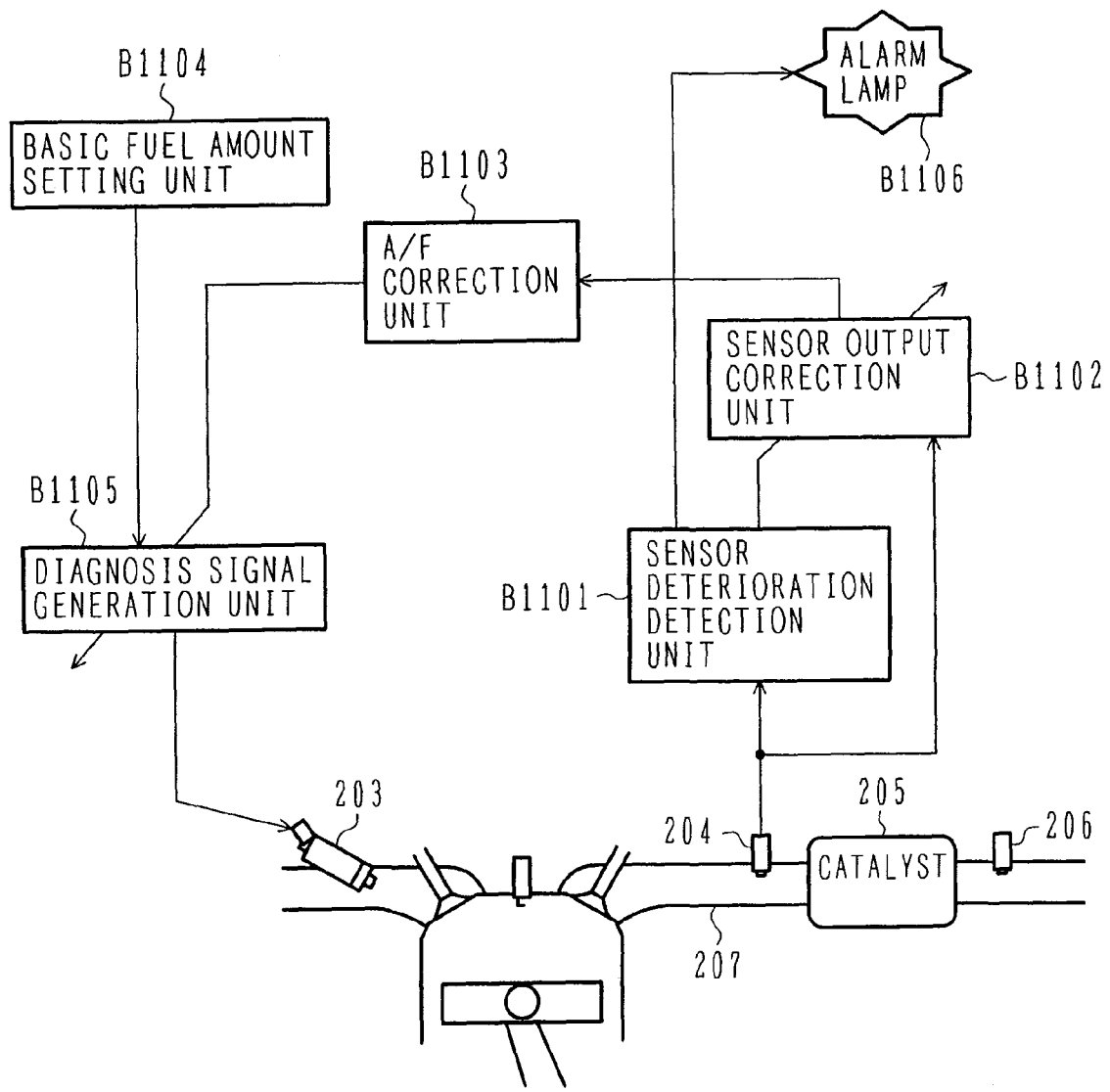
FIG. 11 is a diagram schematically showing the control apparatus for the engine robust against the gain deterioration.

Next, FIG. 11 shows an example of the system for preventing the degradation of the exhaust gas due to the gain deterioration by correcting the sensor. According to the conventional system, the out put of the A/F sensor is directly applied to an A/F correction unit B1103 thereby to correct the A/F of the exhaust gas. In contrast, according to the embodiment shown in FIG. 11, a sensor deterioration detection unit B1101 detects the degree of the gain deterioration, and a sensor output correction unit B1102 corrects the output of the A/F sensor in accordance with the degree of the gain deterioration. For example, when the gain deterioration index becomes half of the normal value, the exhaust gas efficiency similar to that in the normal state can be realized by doubling the detected output of the A/F sensor. When the sensor output is corrected in this manner by using the gain deterioration index, it is possible to constitute the system being robust against the sensor deterioration which can prevent the degradation of the exhaust gas even when the gain deterioration arises. Further, an alarm lamp B1106 is lightened in accordance with the gain deterioration detected by the sensor deterioration detection unit B1101 to notify the occurrence of the abnormality to a driver. In place of the alarm lamp, such an alarm unit capable of outputting a trouble code or lighting a mill may be employed. Alternatively, the abnormality may be notified to a driver by using a voice message. According to such an alarm unit, even when only the gain deterioration representing the abnormality of the detection sensitivity occurs, it is possible to notify the deterioration to a driver.

Second Embodiment

Next, another embodiment of the present invention will be explained with reference to FIGS. 12 to 14.

Figure 12:
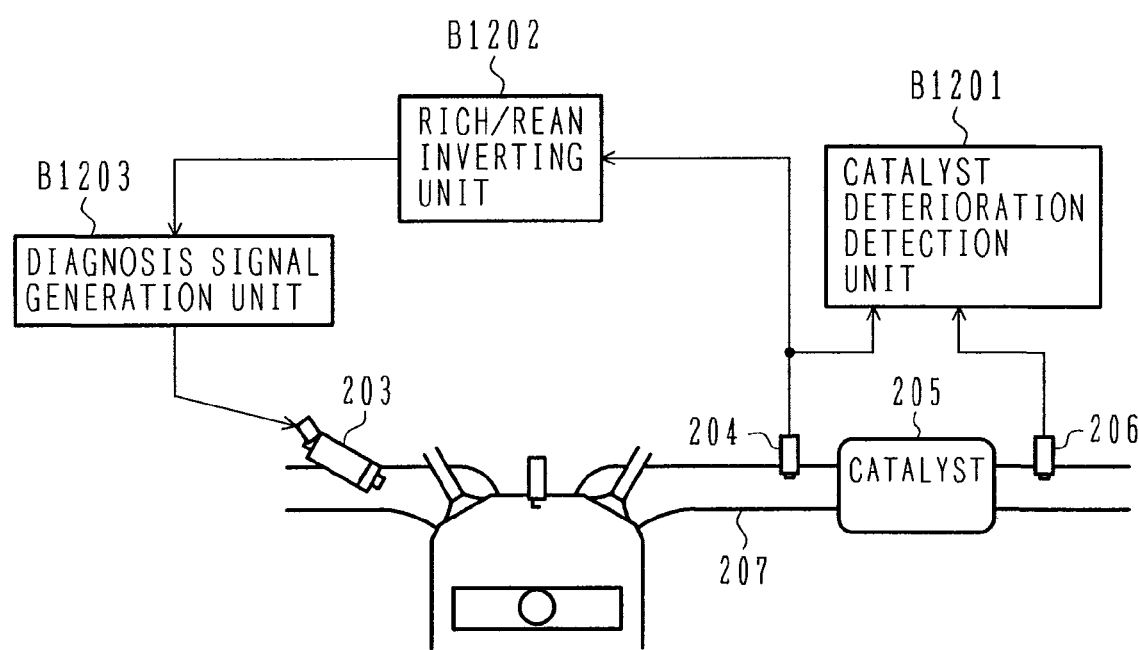
FIG. 12 is a diagram schematically showing the catalyst diagnosis method.

FIG. 12 shows an example of the catalyst diagnosis system. This system includes a unit in which a diagnosis signal generation unit B1203 increases/decreases an amount of the fuel injected from the injectors based on an output of a rich/lean inverting unit B1202 thereby to separately detect the abnormality of the sensor. This system further includes a catalyst deterioration detection unit B1201 which detects the deterioration state of a catalyst based on the outputs of an upstream side linear A/F sensor and a downstream side A/F sensor. As the catalyst deterioration index of the catalyst deterioration detection unit B1201, it is possible to use a ratio of the lengths of loci, a ratio of inversion periods, a ratio of inversion number of times, correlation between the upstream side and downstream side A/F sensors, for example.

Figure 13A:
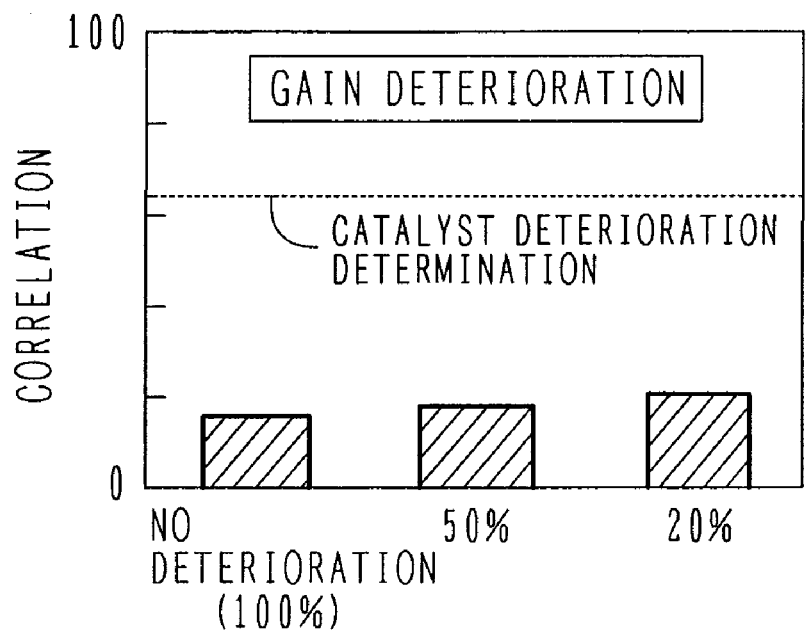
FIGS. 13A and 13B are diagrams showing the experimental result representing the relation between the sensor deterioration and the catalyst diagnosis.
Figure 13B:
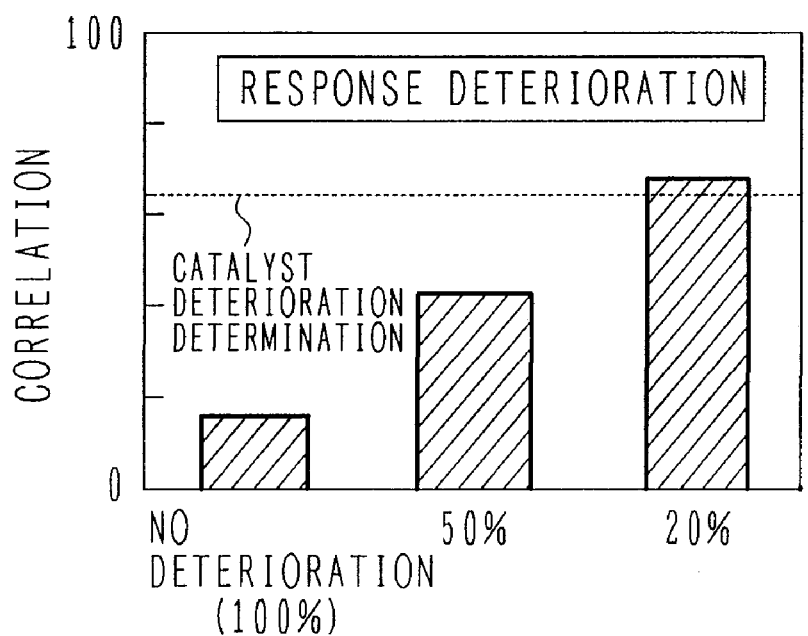

FIGS. 13A and 13B show the experimentation results in which the catalyst deterioration indexes at the time of the deterioration of the sensor were obtained by the experimentations using the catalyst diagnosis system shown in FIG. 12. In this experimentation, the correlation was used as the deterioration index. According to this experimentation, the degree of the degradation of the catalyst increased as the degree of the correlation became larger. This is based on the fact that when the catalyst is degraded, the amplitude of the output of the downstream side A/F sensor becomes large due to the degradation of the oxide absorption ability of the catalyst and so the correlation between the amplitudes of the upstream and downstream side A/F sensors becomes large. The same catalyst was used in all the experimentations. The catalyst deterioration indexes (correlation) were not sensitive for the gain deterioration. In contrast, as to the response deterioration, the deterioration indexes (correlation) increased as the degree of the response deterioration increased. Thus, there arises a case that the catalyst is erroneously determined to be in the deterioration state by the response deterioration even if the catalyst is in the normal state. This is because the inverting period of the rich/lean state becomes longer due to the response deterioration and so the A/F is controlled with a long period exceeding the oxide absorption ability of the normal catalyst. Even in such a state, according to the embodiment, since the output of the sensor is corrected in accordance with the degree of the response deterioration, the erroneous diagnosis can be prevented.

Figure 14:
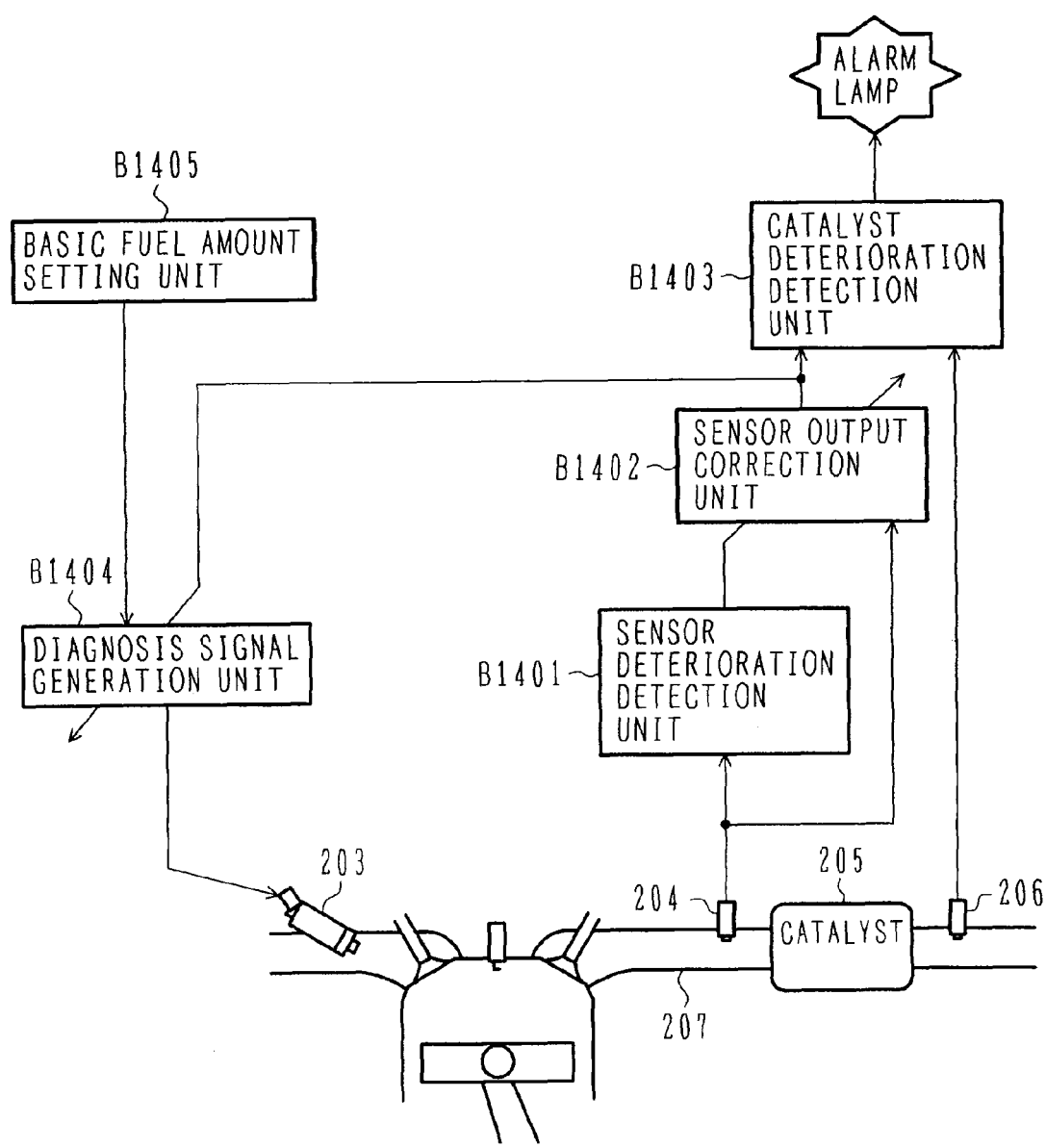
FIG. 14 is a diagram schematically showing the control apparatus for the engine robust against the response deterioration.

FIG. 14 shows an example of the system for preventing the erroneous determination of the catalyst by correcting the sensor output. In this figure, portions having the similar functions as those of FIG. 11 are omitted in their explanation. According to this system, a sensor deterioration detection unit B1401 calculates the response deterioration index to obtain the degree of the response deterioration, and a sensor output correction unit B1402 corrects the output of the A/F sensor in accordance with the response deterioration index. For example, when the sensor output delays in its response by 100 ms with respect to the normal sensor, the response of the linear A/F sensor output is advanced by 100 ms by the phase advance compensation. A catalyst deterioration detection unit B1403 calculates the catalyst deterioration index based on the linear A/F sensor output thus corrected and the output of the downstream side A/F sensor thereby to realize the catalyst deterioration determination system which is robust against the response deterioration.

In the catalyst diagnosis system shown in FIG. 12, since the linear A/F sensor as well as the catalyst can be diagnosed by generating the A/F deviation of 1 Hz or less in the diagnosis signal generation unit B1203, both the reduction of the diagnosis time period and the reduction of the exhaust gas can be realized.

Third Embodiment

Next, a still another embodiment of the present invention will be explained with reference to FIG. 15.

Figure 15:
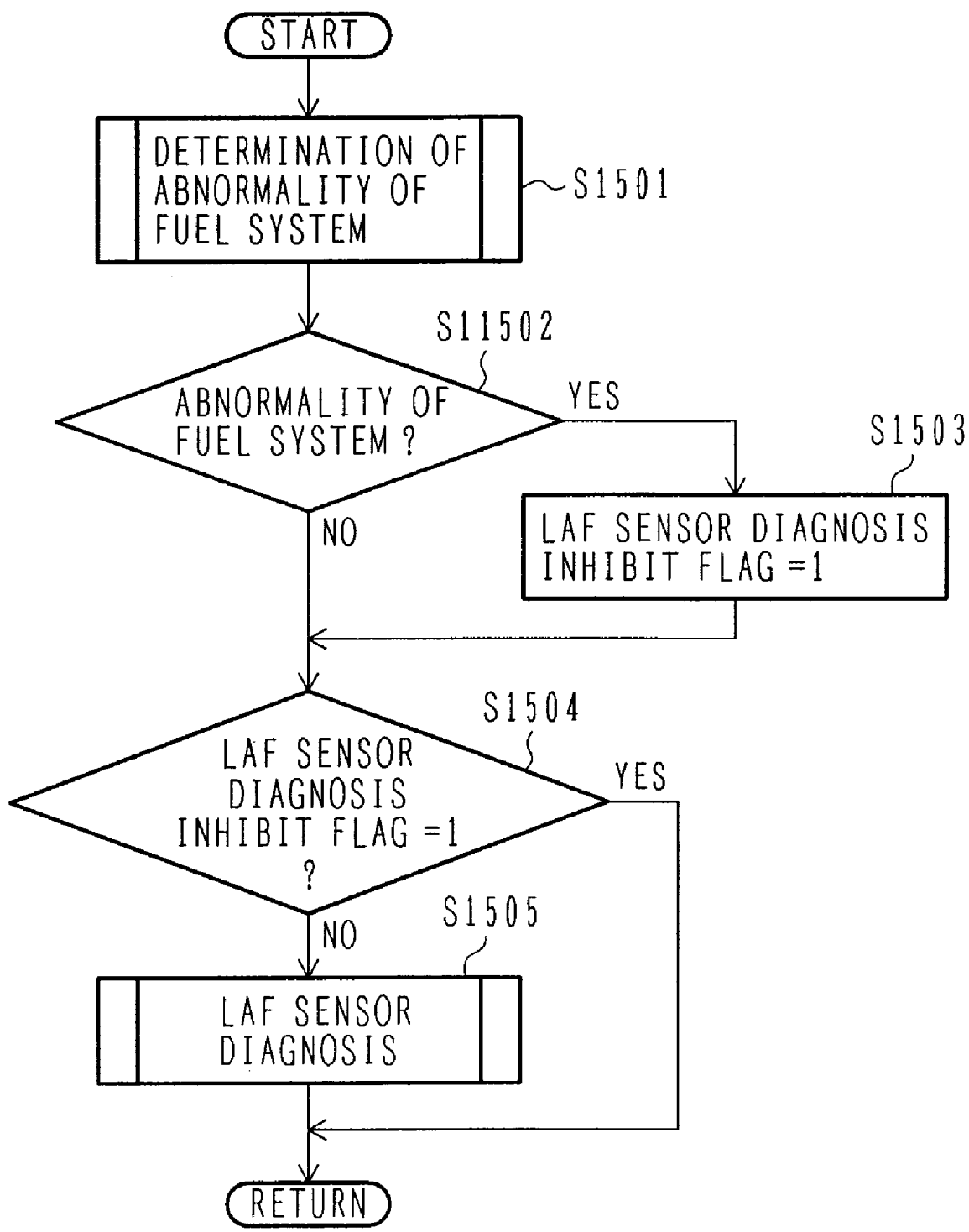
FIG. 15 is a diagram showing a flowchart for explaining the operation of this embodiment in which the diagnosis of the LAF sensor is inhibited when the abnormality of the fuel system is detected.

FIG. 15 shows a flowchart for explaining the operation of this embodiment in which the diagnosis of the LAF sensor is inhibited when the abnormality of the fuel system is detected. In step S1501, it is determined whether or not the fuel system is abnormal. In this case, for example, the fuel system may be determined to be abnormal when an A/F feedback correction coefficient reaches its upper limit or lower limit for a predetermined time period or when an acceleration-pedal opening-degree feedback correction coefficient in the idling operation reaches its upper limit or lower limit for a predetermined time period. In step S1502, it is determined whether or not the fuel system is abnormal. When it is determined that the fuel system is abnormal, the process proceeds to step S1503, whereat an LAF sensor diagnosis inhibit flag is set to 1. In step S1504, it is determined whether or not the LAF sensor diagnosis inhibit flag is 1. When the LAF sensor diagnosis inhibit flag is 1, the process is terminated. In contrast, when the LAF sensor diagnosis is inhibit flag is not 1, the process proceeds to step S1505, whereat the LAF sensor diagnosis explained in the first embodiment, for example, is executed. According to the present invention, when the fuel system is abnormal, the LAF sensor diagnosis is inhibited thereby to prevent the erroneous determination of the LAF sensor diagnosis due to the abnormality of the fuel system.

Figure 16:
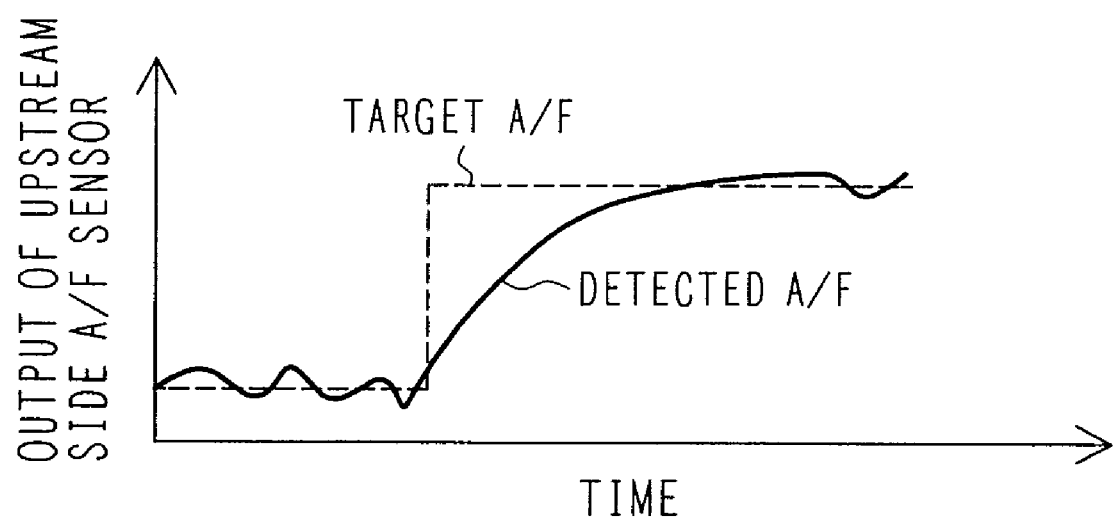
FIG. 16 is a diagram showing another example of the deterioration index according to the embodiment.

In the aforesaid explanation, although the periodical signal shown in FIG. 4A or 4B is used for the LAF sensor diagnosis, the present invention is not limited thereto. For example, not only the periodical signal but also a step-shaped signal as shown in FIG. 16 may be used in the present invention. In this case, when the target A/F is changed in a step manner in the open loop, even when the response deterioration index is set to be a time constant of the detected A/F and the gain deterioration index is set to be an average of the target A/F and the detected A/F after the step change, the response deterioration and the gain deterioration can be detected separately.

What is claimed is:

1. A diagnosis apparatus for an internal combustion engine, comprising:
    a catalyst deterioration diagnosis mode, which detects deterioration of a catalyst based on outputs of a linear A/F sensor and an A/F sensor, the catalyst being disposed within a path of exhaust gas of the engine, the linear A/F sensor being disposed on an upstream side of the catalyst, and the A/F sensor being disposed on a downstream side of the catalyst; and
    a linear A/F sensor deterioration diagnosis mode, in which a frequency of a diagnosis mode for diagnosing the linear A/F sensor is lower than a frequency of a control mode for controlling the A/F;
    wherein both the catalyst deterioration diagnosis mode and the linear A/F sensor deterioration diagnosis mode are carried out.

2. A diagnosis apparatus for an internal combustion engine according to claim 1, wherein the frequency of the A/F deviation of the diagnosis mode for diagnosing the linear A/F sensor in the linear A/F sensor deterioration diagnosis mode is in a range which is equal to or larger than 0 Hz and equal to or less than 1 Hz.

3. A diagnosis apparatus for an internal combustion engine according to claim 1, wherein the frequency of the A/F deviation of the diagnosis mode for diagnosing the linear A/F sensor in the linear A/F sensor deterioration diagnosis mode is in a range which is equal to or larger than 0.3 Hz and equal to or less than 1 Hz.

4. A diagnosis apparatus for an internal combustion engine according to claim 1, wherein both the catalyst deterioration diagnosis mode and the linear A/F sensor deterioration diagnosis mode are carried out simultaneously.

5. A diagnosis apparatus for an internal combustion engine, comprising:
    a catalyst deterioration diagnosis mode, which detects deterioration of a catalyst based on outputs of a linear A/F sensor and an A/F sensor, the catalyst being disposed within a path of exhaust gas of the engine, the linear A/F sensor being disposed on an upstream side of the catalyst, and the A/F sensor being disposed on a downstream side of the catalyst; and
    a linear A/F sensor deterioration diagnosis mode, in which a frequency of a diagnosis mode for diagnosing the linear A/F sensor is lower than a frequency of a control mode for controlling the A/F;
    wherein both the catalyst deterioration diagnosis mode and the linear A/F sensor deterioration diagnosis mode are carried out; and
    wherein it is determined to be the gain deterioration when a gain deterioration index defined by a ratio between a peak value of an A/F detected by the linear A/F sensor and a peak value of the A/F deviation controlled by the linear A/F sensor deterioration diagnosis mode is out of a predetermined range.

6. A diagnosis apparatus for an internal combustion engine according to claim 5, wherein gain characteristics of the linear A/F sensor are corrected based on the gain deterioration index.

7. A diagnosis apparatus for an internal combustion engine, comprising:
    a catalyst deterioration diagnosis mode, which detects deterioration of a catalyst based on outputs of a linear A/F sensor and an A/F sensor, the catalyst being disposed within a path of exhaust gas of the engine, the linear A/F sensor being disposed on an upstream side of the catalyst, and the A/F sensor being disposed on a downstream side of the catalyst; and
    a linear A/F sensor deterioration diagnosis mode, in which a frequency of a diagnosis mode for diagnosing the linear A/F sensor is lower than a frequency of a control mode for controlling the A/F;
    wherein both the catalyst deterioration diagnosis mode and the linear A/F sensor deterioration diagnosis mode are carried out; and
    wherein it is determined to be the response deterioration when a response deterioration index defined by a ratio between a period of an A/F detected by the linear A/F sensor and a period of the A/F deviation controlled by the linear A/F sensor deterioration diagnosis mode is larger than a predetermined value.

8. A diagnosis apparatus for an internal combustion engine according to claim 7, wherein gain characteristics of the linear A/F sensor are corrected based on the response deterioration index.

9. A diagnosis apparatus for an internal combustion engine according to claim 1, wherein the diagnosis of the linear A/F sensor is inhibited when an abnormality of a fuel system of the engine is detected.

* * * * *